United States Patent
Jeon et al.

(10) Patent No.: US 9,818,212 B2
(45) Date of Patent: Nov. 14, 2017

(54) MAGNETIC RESONANCE IMAGING (MRI) APPARATUS AND METHOD OF PROCESSING MR IMAGE

(71) Applicant: SAMSUNG ELECTRONICS CO., LTD., Suwon-si (KR)

(72) Inventors: Seun Jeon, Montreal (CA); Jun-sung Park, Seoul (KR); Jong-min Lee, Seoul (KR); Jun-ki Lee, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 94 days.

(21) Appl. No.: 14/886,657

(22) Filed: Oct. 19, 2015

(65) Prior Publication Data
US 2016/0110904 A1    Apr. 21, 2016

(30) Foreign Application Priority Data

Oct. 21, 2014 (KR) .................. 10-2014-0142782

(51) Int. Cl.
*G06K 9/00* (2006.01)
*G06T 11/60* (2006.01)
(Continued)

(52) U.S. Cl.
CPC .......... *G06T 11/60* (2013.01); *A61B 5/0042* (2013.01); *A61B 5/055* (2013.01); *A61B 5/4076* (2013.01);
(Continued)

(58) Field of Classification Search
CPC . G06T 11/60; G06T 2207/10088; G06T 7/11; G06T 7/174; G06T 2207/30016;
(Continued)

(56) References Cited

U.S. PATENT DOCUMENTS

| 7,995,825 B2 | 8/2011 | Jack et al. |
| 9,247,894 B2 | 2/2016 | Kato |
| 2013/0129168 A1* | 5/2013 | Ross ............... G06T 7/0012 382/128 |

FOREIGN PATENT DOCUMENTS

| JP | 2005-118510 A | 5/2005 |
| JP | 5458453 B2 | 4/2014 |

(Continued)

OTHER PUBLICATIONS

Wei Wen et al; "The topography of white matter hyperintensities on brain MRI in healthy 60- to 64-year-old individuals"; Neuroimage; vol. 22; 2004; pp. 144-154.*

(Continued)

*Primary Examiner* — Gregory F Cunningham
(74) *Attorney, Agent, or Firm* — Sughrue Mion, PLLC

(57) ABSTRACT

A magnetic resonance imaging (MRI) apparatus and a method of processing an MR image are provided. The MRI apparatus includes a scanner configured to acquire a first image that is a T1-weighted image and a second image that is a fluid attenuated inversion recovery (FLAIR) image by performing an MRI scan on a brain. The MRI apparatus further includes an image processor configured to determine a white matter region in the second image based on the first image and the second image, and detect a white matter hyperintensity (WMH) region in the determined white matter region. The MRI apparatus further includes an output interface configured to display the detected WMH region and a change in the WMH region over time.

18 Claims, 11 Drawing Sheets

(51) Int. Cl.
A61B 5/055 (2006.01)
G06T 7/11 (2017.01)
G06T 7/174 (2017.01)
A61B 5/00 (2006.01)

(52) U.S. Cl.
CPC ............... *G06T 7/11* (2017.01); *G06T 7/174* (2017.01); *A61B 5/7425* (2013.01); *A61B 5/7475* (2013.01); *G06T 2207/10088* (2013.01); *G06T 2207/30016* (2013.01)

(58) Field of Classification Search
CPC ..... A61B 5/055; A61B 5/7475; A61B 5/7425; A61B 5/4076; A61B 5/0042
USPC ......................................................... 382/131
See application file for complete search history.

(56) References Cited

FOREIGN PATENT DOCUMENTS

| KR | 10-2009-0111160 A | 10/2009 |
|---|---|---|
| KR | 10-2014-0001294 A | 1/2014 |
| WO | 2009003198 A1 | 12/2008 |
| WO | 2011040473 A1 | 4/2011 |
| WO | 2013086026 A1 | 6/2013 |

OTHER PUBLICATIONS

Communication dated Jun. 1, 2016 issued by the Korean Intellectual Property Office in counterpart Korean Application No. 10-2014-0142782.

Communication dated Aug. 10, 2016 issued by the Korean Intellectual Property Office in counterpart Korean Patent Application No. 10-2014-0142782.

Mitsuhiro Yoshita, et al; "Current Concepts of Analysis of Cerebral White Matter Hyperintensities on Magnetic Resonance Imaging"; Top Magn Reson Imaging; vol. 16; No. 6; Dec. 2005; pp. 399-407; Author Manuscript: NIH Public Access; pp. 1-18.

Jeon et al., "Fully Automated Pipeline for Quantification and Localization of White Matter Hyperintensity in Brain Magnetic Resonance Image", Dec. 31, 2010, 8 pages total, Seoul, South Korea.

Communication dated Jan. 5, 2016 issued by the Korean Intellectual Property Office in counterpart Korean Patent Application No. 10-2014-0142782.

* cited by examiner

FIG. 4

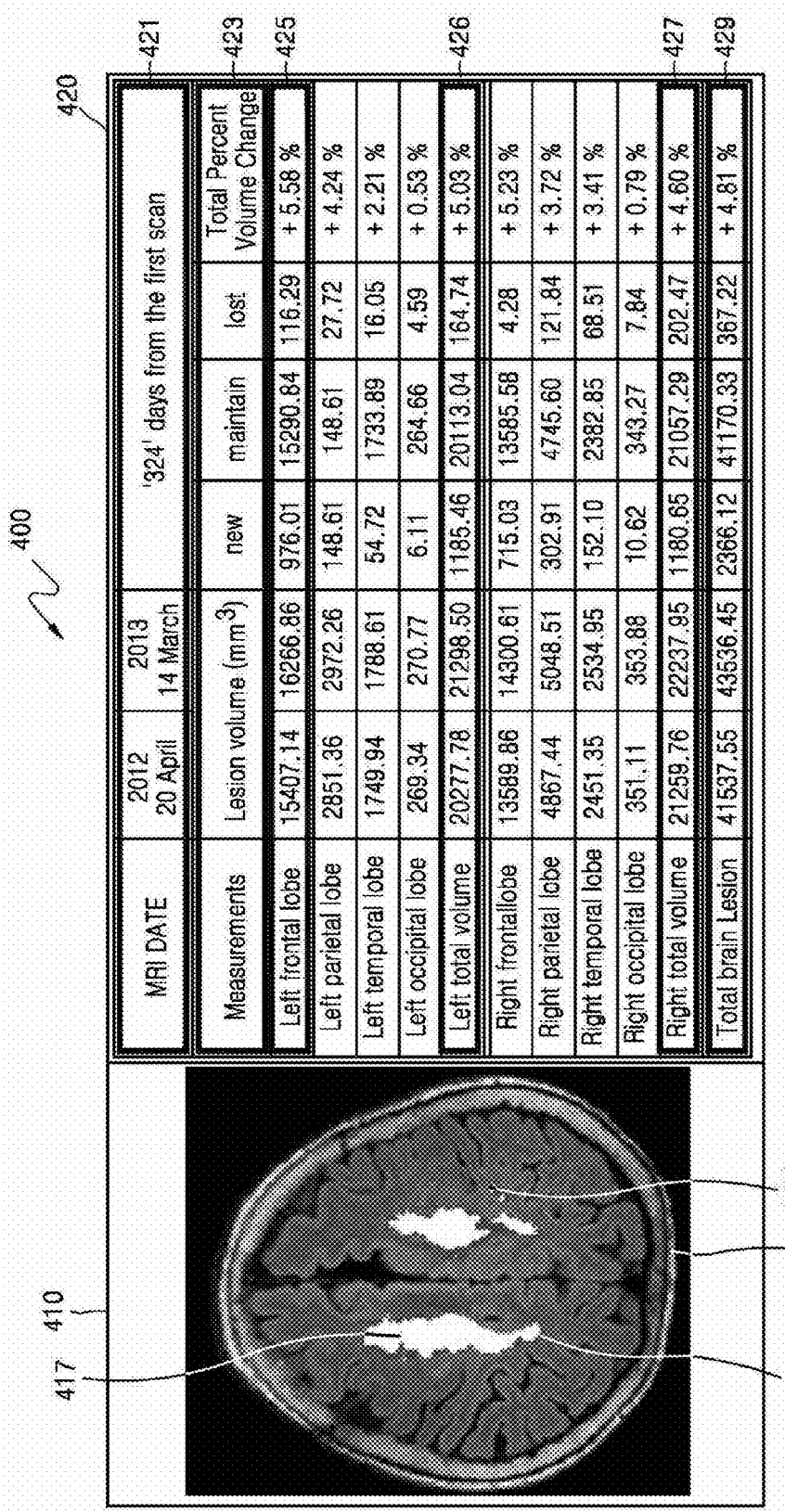

| MRI DATE | 2012 20 April | 2013 14 March | '324' days from the first scan | | |
|---|---|---|---|---|---|
| Measurements | Lesion volume (mm³) | | new | maintain | lost | Total Percent Volume Change |
| Left frontal lobe | 15407.14 | 16266.86 | 976.01 | 15290.84 | 116.29 | + 5.58 % |
| Left parietal lobe | 2851.36 | 2972.26 | 148.61 | 148.61 | 27.72 | + 4.24 % |
| Left temporal lobe | 1749.94 | 1788.61 | 54.72 | 1733.89 | 16.05 | + 2.21 % |
| Left occipital lobe | 269.34 | 270.77 | 6.11 | 264.66 | 4.59 | + 0.53 % |
| Left total volume | 20277.78 | 21298.50 | 1185.46 | 20113.04 | 164.74 | + 5.03 % |
| Right frontal lobe | 13589.86 | 14300.61 | 715.03 | 13585.58 | 4.28 | + 5.23 % |
| Right parietal lobe | 4867.44 | 5048.51 | 302.91 | 4745.60 | 121.84 | + 3.72 % |
| Right temporal lobe | 2451.35 | 2534.95 | 152.10 | 2382.85 | 68.51 | + 3.41 % |
| Right occipital lobe | 351.11 | 353.88 | 10.62 | 343.27 | 7.84 | + 0.79 % |
| Right total volume | 21259.76 | 22237.95 | 1180.65 | 21057.29 | 202.47 | + 4.60 % |
| Total brain Lesion | 41537.55 | 43536.45 | 2366.12 | 41170.33 | 367.22 | + 4.81 % |

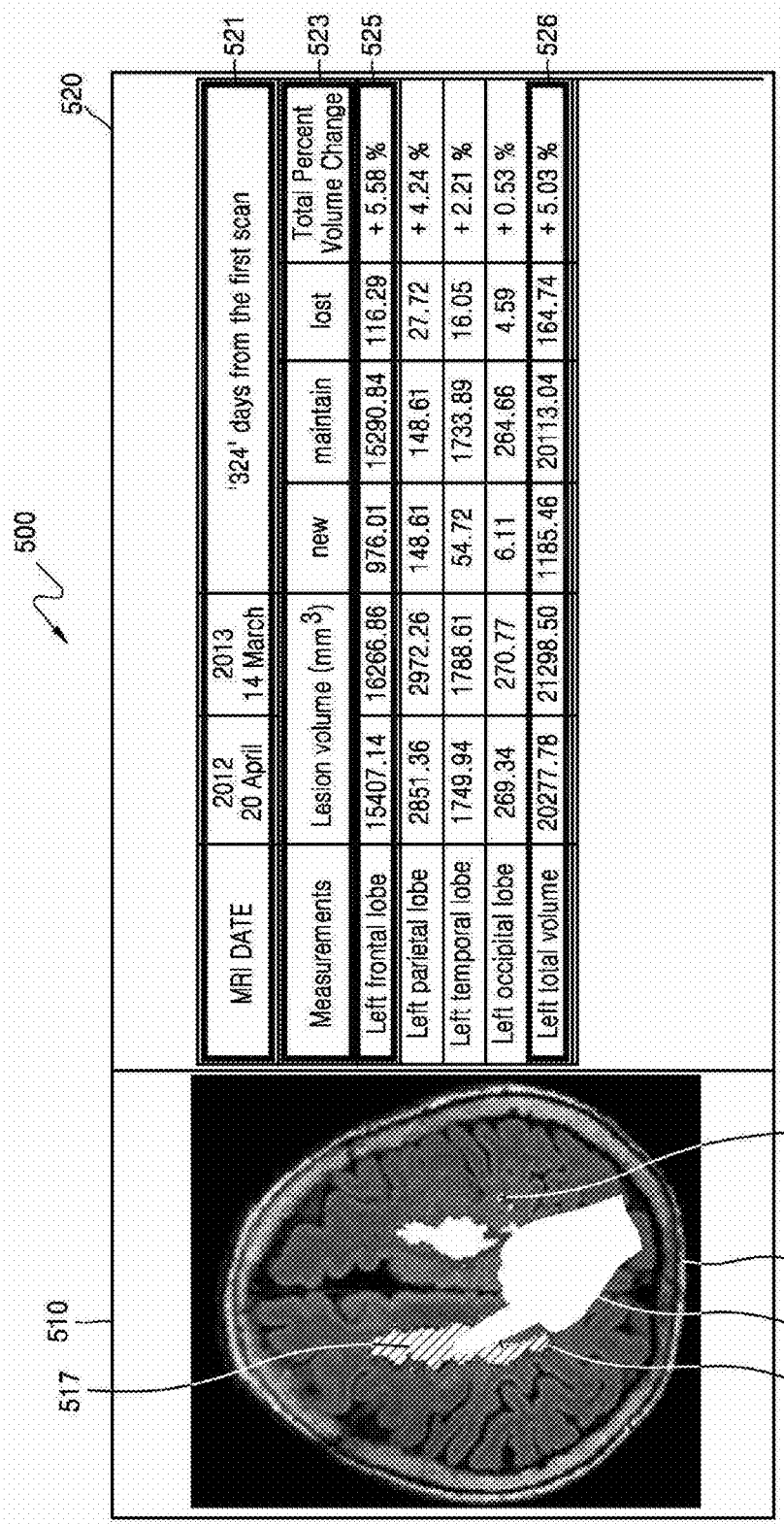

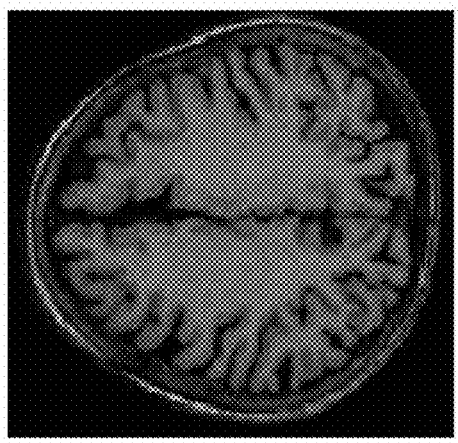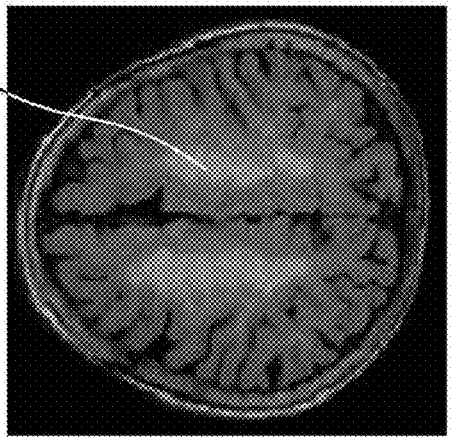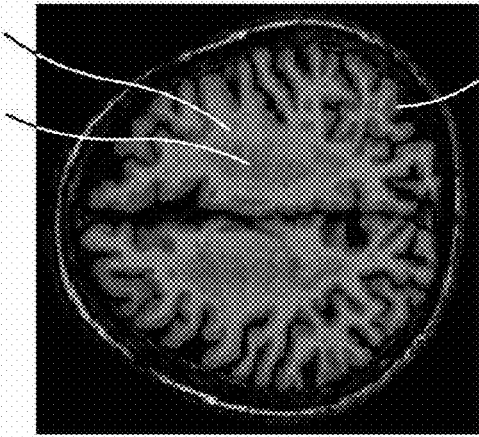

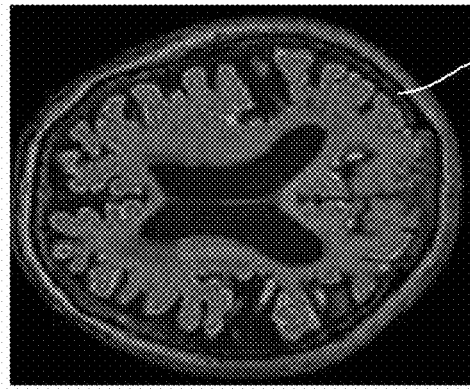
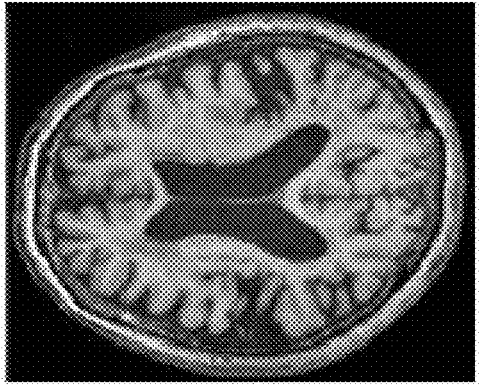

MAGNETIC RESONANCE IMAGING (MRI) APPARATUS AND METHOD OF PROCESSING MR IMAGE

CROSS-REFERENCE TO RELATED APPLICATION

This application claims priority from Korean Patent Application No. 10-2014-0142782, filed on Oct. 21, 2014, in the Korean Intellectual Property Office, the disclosure of which is incorporated herein in its entirety by reference.

BACKGROUND

1. Field

Apparatuses and methods consistent with exemplary embodiments relate to a magnetic resonance imaging (MRI) apparatus and a method of processing an MR image.

2. Description of the Related Art

An MRI apparatus uses a magnetic field to capture an image of a subject, and is widely used in the accurate diagnosis of diseases because it shows stereoscopic images of bones, lumbar discs, joints, nerve ligaments, the heart, etc., at angles.

To detect a white matter hyperintensity (WMH) region located in a white matter area of the brain, the white matter area may be defined first in an image of the brain. Then, the WMH region may be determined in the defined white matter area.

Furthermore, to assess a degree of improvement or worsening of a patient's symptoms, images of a WMH region captured at predetermined time intervals may be compared with one another. In this case, signal intensity may vary according to an imaging environment and the type of an imaging apparatus. Thus, to observe a change in the WMH region over time, signal intensities on images acquired during an MRI scan may be normalized based on criteria.

SUMMARY

Exemplary embodiments may address at least the above problems and/or disadvantages and other disadvantages not described above. Also, the exemplary embodiments are not required to overcome the disadvantages described above, and an exemplary embodiment may not overcome any of the problems described above.

One or more exemplary embodiments include a magnetic resonance imaging (MRI) apparatus and a method of processing an MR image whereby a white matter hyperintensity (WMH) region may be detected more accurately by using a Fluid Attenuated Inversion Recovery (FLAIR) image and a T1 weighted image in which a gray matter region is distinctly separated from a white matter region.

One or more exemplary embodiments include an MRI apparatus and a method of processing an MR image whereby a degree of change in a WMH region over time may be precisely detected by normalizing signal intensity in an MR image over time.

According to an aspect of an exemplary embodiment, an MRI apparatus includes a scanner configured to acquire a first image that is a T1-weighted image and a second image that is a fluid attenuated inversion recovery (FLAIR) image by performing an MRI scan on a brain. The MRI apparatus further includes an image processor configured to determine a white matter region in the second image based on the first image and the second image, and detect a white matter hyperintensity (WMH) region in the determined white matter region. The MRI apparatus further includes an output interface configured to display the detected WMH region and a change in the WMH region over time.

The scanner may be configured to acquire the first image and the second image at a first time point, and acquire the first image and the second image at a second time point later than the first time point, and the output interface may be configured to display a generation and a loss of the WMH region over time between the first time point and the second time point.

The output interface may be configured to indicate portions where the WMH region is generated and lost at corresponding locations in the second image.

The output interface may be configured to display the second image in a first region of a screen, and display, as numerical values, a volume of the WMH region and an amount of change in the WMH region over time, in a second region of the screen.

The change in the WMH region over time may include a change over time in the WMH region in at least one among frontal, parietal, temporal, and occipital lobes.

The MRI apparatus may further include an input interface configured to receive an input selecting at least one among frontal, parietal, temporal, and occipital lobes.

The output interface may be configured to display a change over time in the WMH region in the selected at least one among frontal, parietal, temporal, and occipital lobes.

The image processor may be configured to generate a blended image by performing a weighted sum on the first image and the second image, and determine the white matter region based on the blended image.

The scanner may be configured to acquire the first image and the second image at a first time point, and acquire the first image and the second image at a second time point later than the first time point, and the image processor may be configured to normalize an intensity of an image signal in each of the second image acquired at the first time point and the second image acquired at the second time point.

The image processor may be configured to normalize the intensity of the image signal based on an intensity of an image signal in a gray matter region in each of the second image acquired at the first time point and the second image acquired at the second time point.

According to an aspect of another exemplary embodiment, there is provided a method of processing a magnetic resonance (MR) image, the method including acquiring a first image that is a T1-weighted image and a second image that is a fluid attenuated inversion recovery (FLAIR) image by performing a magnetic resonance imaging (MRI) scan on a brain, determining a white matter region in the second image based on the first image and the second image, detecting a white matter hyperintensity (WMH) region in the determined white matter region, and displaying the detected WMH region and a change in the WMH region over time.

The acquiring may include acquiring the first image and the second image at a first time point, and acquiring the first image and the second image at a second time point later than the first time point, and the displaying may include displaying a generation and a loss of the WMH region over time between the first time point and the second time point.

The displaying may include indicating portions where the WMH region is generated and lost at corresponding locations in the second image.

The displaying may include displaying the second image in a first region of a screen, and displaying, as numerical values, a volume of the WMH region and an amount of change in the WMH region over time, in a second region of the screen.

The method may further include receiving an input selecting at least one among the frontal, parietal, temporal, and occipital lobes.

The displaying may include displaying a change over time in the WMH region in the selected at least one among frontal, parietal, temporal, and occipital lobes.

The determining may include generating a blended image by performing a weighted sum on the first image and the second image, and determining the white matter region based on the blended image.

The determining may include classifying tissues in the blended image, the tissues including another white matter region, generating a white matter region image including the other white matter region, and overlaying the whiter matter region image over the second image to determine the white matter region in the second image.

The acquiring may include acquiring the first image and the second image at a first time point, and acquiring the first image and the second image at a second time point later than the first time point, and the detecting may include normalizing an intensity of an image signal in each of the second image acquired at the first time point and the second image acquired at the second time point.

The normalizing may include normalizing the intensity of the image signal based on an intensity of an image signal in a gray matter region in each of the second image acquired at the first time point and the second image acquired at the second time point.

BRIEF DESCRIPTION OF THE DRAWINGS

The above and/or other aspects will become more apparent by describing exemplary embodiments with reference to the accompanying drawings, in which:

FIG. 4 is a screen for processing an MR image, according to an exemplary embodiment;

FIG. 5 is a screen for processing an MR image, according to another exemplary embodiment;

FIGS. 6A, 6B, 6C, 7A, 7B, 7C, 8A, 8B, 8C, 9A, 9B, and 9C are diagrams illustrating processing of an MR image, according to an exemplary embodiment;

DETAILED DESCRIPTION

Figure 1:
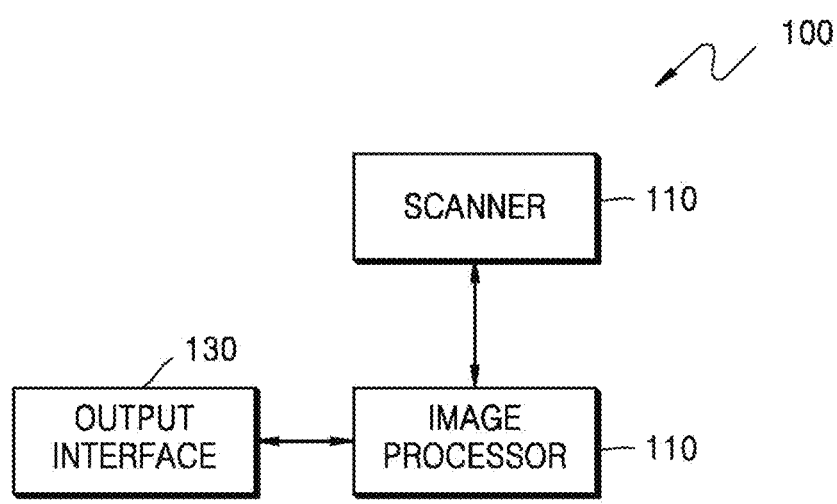
FIG. 1 is a block diagram of a magnetic resonance imaging (MRI) apparatus according to an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments may be practiced without those specifically defined matters. Also, well-known functions or constructions may not be described in detail because they would obscure the description with unnecessary detail.

In the present specification, an "image" may refer to multi-dimensional data composed of discrete image elements (e.g., pixels in a two-dimensional (2D) image and voxels in a three-dimensional (3D) image). For example, the image may be a medical image of an object captured by an X-ray apparatus, a computed tomography (CT) apparatus, a magnetic resonance imaging (MRI) apparatus, an ultrasound diagnosis apparatus, or another medical imaging apparatus.

Furthermore, in the present specification, an "object" may be a human, an animal, or a part of a human or animal. For example, the object may be an organ (e.g., the liver, the heart, the womb, the brain, a breast, or the abdomen), a blood vessel, or a combination thereof. Furthermore, the "object" may be a phantom. The phantom is a material having a density, an effective atomic number, and a volume that are approximately the same as those of an organism. For example, the phantom may be a spherical phantom having properties similar to the human body.

Furthermore, in the present specification, a "user" may be, but is not limited to, a medical expert, such as a medical doctor, a nurse, a medical laboratory technologist, or a technician who repairs a medical apparatus.

Furthermore, in the present specification, an "MR image" refers to an image of an object obtained by using the nuclear magnetic resonance principle.

Furthermore, in the present specification, a "pulse sequence" refers to continuity of signals repeatedly applied by an MRI apparatus. The pulse sequence may include a time parameter of a radio frequency (RF) pulse, for example, repetition time (TR) or echo time (TE).

Furthermore, in the present specification, a "pulse sequence schematic diagram" shows an order of events that occur in an MRI apparatus. For example, the pulse sequence schematic diagram may be a diagram showing an RF pulse, a gradient magnetic field, an MR signal, or the like according to time.

An MRI system is an apparatus for acquiring a sectional image of a part of an object by expressing, in a contrast comparison, a strength of a MR signal with respect to a radio frequency (RF) signal generated in a magnetic field having a strength. For example, if an RF signal that only resonates an atomic nucleus (for example, a hydrogen atomic nucleus) is emitted for an instant toward the object placed in a strong magnetic field and then such emission stops, an MR signal is emitted from the atomic nucleus, and thus the MRI system may receive the MR signal and acquire an MR image. The MR signal denotes an RF signal emitted from the object. An intensity of the MR signal may be determined according to a density of a predetermined atom (for example, hydrogen) of the object, a relaxation time T1, a relaxation time T2, and a flow of blood or the like.

MRI systems include characteristics different from those of other imaging apparatuses. Unlike imaging apparatuses such as CT apparatuses that acquire images according to a direction of detection hardware, MRI systems may acquire 2D images or 3D volume images that are oriented toward an optional point. MRI systems do not expose objects or examiners to radiation, unlike CT apparatuses, X-ray apparatuses, position emission tomography (PET) apparatuses, and single photon emission CT (SPECT) apparatuses, may acquire images having high soft tissue contrast, and may acquire neurological images, intravascular images, musculoskeletal images, and oncologic images that are used to precisely capture abnormal tissues.

FIG. 1 is a block diagram of an MRI apparatus 100 according to an exemplary embodiment.

The MRI apparatus 100 may be a device that performs an MRI scan of an object and processes an image acquired using the MRI scan.

Referring to FIG. 1, the MRI apparatus 100 according to an exemplary embodiment includes a scanner 110, an image processor 120, and an output interface 130.

The scanner 110 may perform an MRI scan of the brain to acquire a first image that is a T1-weighted image and a second image that is a Fluid Attenuated Inversion Recovery (FLAIR) image. Hereinafter, the first and second images represent a T1-weighted image and a FLAIR image, respectively.

The scanner 110 may acquire first and second images at predetermined time intervals to display a change in a white matter hyperintensity (WMH) region over time. In detail, the scanner 110 may acquire both the first and second images at a first time point and then again at a second time point that is later than the first time point. The first and second time points correspond to time points when MRI scans were performed on a patient. A time interval between the first and second time points may be years, months, etc., but is not limited thereto.

The image processor 120 determines a white matter region in the second image based on the first and second images, and detects a WMH region in the white matter region.

The image processor 120 may determine the white matter region based on the first and second images acquired at the first time point, and detect the WMH region in the determined white matter region corresponding to the first time point. Similarly, the image processor 120 may determine a white matter region based on the first and second images acquired at the second time point, and detect the WMH region in the determined white matter region corresponding to the second time point.

A method of determining a white matter region and detecting a WMH region will be described in more detail below with reference to FIGS. 6A through 9C.

The output interface 130 may display a detected WMH region and a change in the WMH region over time. The output interface 130 may display a change (e.g., new formation, loss, etc.) in WMH over time between the first and second time points, based on WMH regions corresponding to the first and second time points.

A method of displaying a change in a WMH region over time will be described in more detail with reference to FIGS. 4 and 5.

Figure 2:
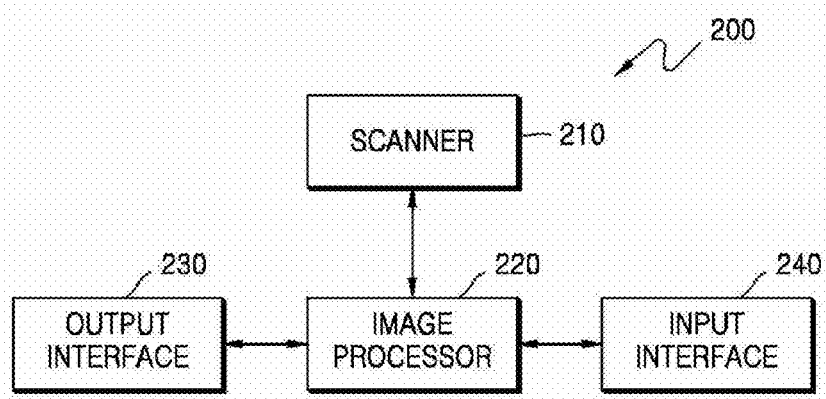
FIG. 2 is a block diagram of an MRI apparatus according to another exemplary embodiment.

FIG. 2 is a block diagram of an MRI apparatus 200 according to another exemplary embodiment.

Referring to FIG. 2, the MRI apparatus 200 according to an exemplary embodiment includes a scanner 210, an image processor 220, an output interface 230, and an input interface 240. Because the scanner 210, the image processor 220, and the output interface 230 may correspond to the scanner 110, the image processor 120, and the output interface 130 shown in FIG. 1, detailed descriptions thereof are omitted.

Unlike in the MRI apparatus 100, the MRI apparatus 200 further includes the input interface 240.

The input interface 240 may be a unit via which the user inputs data for controlling the MRI apparatus 200. According to an exemplary embodiment, the input interface 240 receives a user input for selecting a portion from an image.

For example, the input interface 240 may receive a user input for selecting at least one among a frontal lobe, a parietal lobe, a temporal lobe, and an occipital lobe of a cerebrum. The user input may be performed by clicking a mouse button, touching a touch screen, pressing a key on a keyboard, etc., but is not limited thereto.

According to an exemplary embodiment, the user input may be a touch via a touch screen or a mouse click on a portion corresponding to at least one among the frontal lobe, the parietal lobe, the temporal lobe, and the occipital lobe in a second image displayed on a first region of a screen. The output interface 230 may display a change over time in a WMH region on the portion selected based on the user input.

The input interface 240 includes a key pad, a dome switch, a touch screen, a touch pad, a jog wheel, a jog switch, etc.

Figure 3:
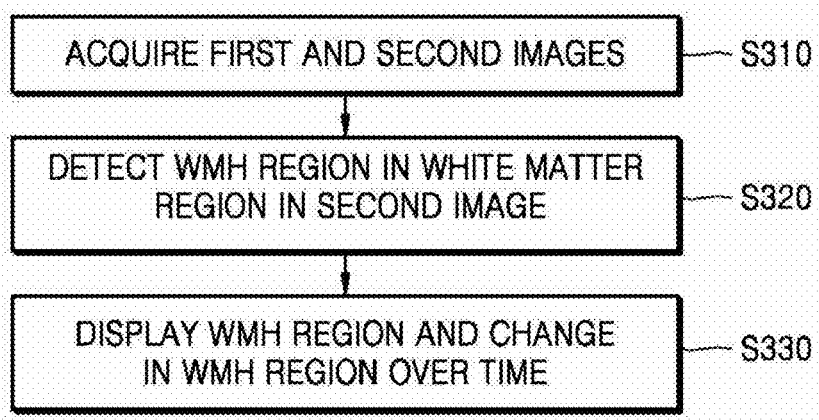
FIG. 3 is a flowchart of a method of processing an MR image, according to an exemplary embodiment.

FIG. 3 is a flowchart of a method of processing an MR image, according to an exemplary embodiment.

Referring to FIG. 3, the MRI apparatus 100 (200) may perform an MRI scan on the brain to acquire a first image that is a T1-weighted image and a second image that is a FLAIR image (S310). In this case, the MRI apparatus 100 (200) may acquire both the first and second images at a predetermined time period. In detail, the MRI apparatus 100 (200) may acquire the first and second images at a first time point and acquire the first and second images again at a second time point that is later than the first time point.

The MRI apparatus 100 (200) determines a white matter region in the acquired second image, and detects a WMH region in the determined white matter region in the acquired second image (S320). In detail, in operation S320, the MRI apparatus 100 (200) may determine a white matter region based on the first and second images acquired at the first time point. The MRI apparatus 100 (200) may then detect a WMH region in the determined white matter region corresponding to the first time point. Furthermore, in operation S320, the MRI apparatus 100 (200) may determine a white matter region based on the first and second images acquired at the second time point. The MRI apparatus 100 (200) may then detect a WMH region in the determined white matter region corresponding to the second time point.

Thereafter, the MRI apparatus 100 (200) displays the detected WMH region and a change in the WMH region over time (S330).

FIG. 4 is a screen 400 for processing an MR image, according to an exemplary embodiment.

A second image 411 of the brain may be displayed on a first region 410 of the screen 400. An image that is displayed on the first region 410 is not limited to the second image and may be a T1-weighted image, a T2-weighted image, or various other types of images. For convenience, it is assumed hereinafter that the second image is displayed on the first region 410 of the screen 400.

A change in a WMH region over time may be displayed on the first region 410 by comparing a WMH region corresponding to a first time point with a WMH region corresponding to a second time point that is later than the first time point. Referring to FIG. 4, on the first region 410, a portion where a WMH region is maintained, a portion where a WMH region is newly formed, and a portion where a WMH region is lost may be indicated on their corresponding portions in the second image 411. For example, the portion where a WMH region is maintained, the portion where a WMH region is newly formed, and the portion where a WMH region is lost may be indicated in white 417, red 413, and blue 415, respectively.

A volume of a WMH region and the amount of change in the volume of the WMH region over time may be displayed on a second region 420 of the screen 400 as numerical values.

The volume of the WMH region for each of the frontal, parietal, temporal, and occipital lobes may be displayed on the second region 420 of the screen 400. The amount of change in the volume of WMH region over time may also be displayed on the second region 420 for each of the frontal, parietal, temporal, and occipital lobes.

Furthermore, the volume of the WMH region may be displayed on the second region 420 for left and right sides of the brain.

Referring to FIG. 4, measurements of the volume of the WMH region for the left side of the brain may be represented in a table where the volume of the WMH region for the left side of the brain is divided into a left frontal lobe volume, a left parietal lobe volume, a left temporal lobe volume, a left occipital lobe volume, and a left total volume. Furthermore, similarly, measurements of the volume of WMH region for the right side of the brain may be illustrated in the table where the volume of WMH region for the right side of the brain is divided into a right frontal lobe volume, a right parietal lobe volume, a right temporal lobe volume, a right occipital lobe volume, and a right total volume.

An MRI date is indicated on a first row 421 of the table displayed on the second region 420. As shown in FIG. 4, a first time point that is the first MRI date and a second time point that is later than the first MRI date may be indicated as Apr. 20, 2012, and Mar. 14, 2013, respectively. In this case, a time interval between the first and second time points may be indicated as '324' days.

Measurement items of numerical values may be indicated on a second row of the table 423 on the second region 420. In detail, a lesion volume, a newly formed lesion (denoted by 'new'), a maintained lesion (denoted by 'maintain'), a lost lesion (denoted by 'lost'), and a total percent of volume change may be indicated on the second row 423 corresponding to measurements. Volumes of white matter lesions in the left frontal lobe at the first and second time points (15407.14 and 16266.86, respectively), volumes of white matter lesions newly formed, maintained, and lost in the left frontal lobe (976.01, 15290.84, and 116.29, respectively), and a total percent of volume change in a white matter lesion found in the left frontal lobe (+5.58%) are sequentially indicated on a third row 425 corresponding to the left frontal lobe. Like on the third row 425, numerical values for the other lobes may be sequentially indicated on subsequent rows. Numerical values for a total volume of white matter lesions in the left side of the brain ('left total volume') may be indicated on a seventh row 426. Similarly, numerical values for a total volume of white matter lesions in the right side of the brain ('right total volume') may be indicated on a twelfth row 427. Numerical values for a total volume of white matter lesions in the whole brain ('total brain lesion') may be indicated on a thirteenth row 429.

According to an exemplary embodiment, the user may identify a change in a WMH region over time by examining the first region 410 of the screen 400. Furthermore, the user may quantitatively analyze a volume of a WMH region in each portion of the brain and a change in volume of the WMH region, thereby allowing quick, precise diagnosis.

FIG. 5 is a screen 500 for processing an MR image, according to another exemplary embodiment.

FIG. 5 illustrates an example where numerical values for a portion selected from a first region 510 of the screen 500 via a user input are displayed on a second region 520 of the screen 500.

As described above with reference to FIG. 4, a second image 511 of a brain may be displayed on the first region 510 of the screen 500. A volume of a WMH region and the amount of change in the volume of the WMH region over time may be displayed on the second region 520 as numerical values. Descriptions of items displayed on the screen 500 that are already provided above with respect to the items displayed on the screen 400 will be omitted below.

The user may select at least one among frontal, parietal, temporal, and occipital lobes via the input interface 240. Furthermore, the user may select one of the left and right sides of the brain via the input interface 240.

For convenience, FIG. 5 shows that a user input 501 is an input via which a portion corresponding to the left side of the brain is selected from the first region 510, but exemplary embodiments are not limited thereto.

The output interfaces 130 and 230 shown in FIGS. 1 and 2, respectively, may display a change over time in a WMH region on the portion selected based on the user input 501. According to an exemplary embodiment, as shown in FIG. 5, a change over time in a WMH region located in each portion of the brain may be displayed on the first region 510. In another exemplary embodiment, only a change over time in a WMH region on the portion selected via the user input 501 may be indicated on its corresponding portion on the first region 510. For example, if the user input 501 is an input for selecting the left side of the brain, portions 513, 515, and 517 where a WMH region is lost, newly formed, and maintained, respectively, may be indicated only on the left side of the brain on the first region 510.

A volume of a WMH region in the left side of the brain and the amount of change in the volume of the WMH region over time may be displayed on the second region 520 as numerical values. In other words, numerical values for the left side of the brain were indicated in a first row 521 through a seventh row 526 of a table on the second region 520. The numerical values may correspond to data indicated on the first row 421 through the seventh row 426 of the table on the second region 420 shown in FIG. 4.

According to an exemplary embodiment, the user may represent a change in WMH region over time by displaying the change on the first region 510 of the screen 500. Furthermore, the user may select a portion to be precisely analyzed to quantitatively view numerical values on the second region 520.

FIGS. 6A, 6B, 6C, 7A, 7B, 7C, 8A, 8B, 8C, 9A, 9B, and 9C are diagrams illustrating processing of an MR image, according to an exemplary embodiment.

FIGS. 6A and 6B respectively illustrate a T1-weighted image 610 acquired at a first time point and a FLAIR image 620 acquired at the first time point. FIG. 6C shows a blended image 630 generated by performing a weighted sum operation on the T1-weighted image 610 and the FLAIR image 620 acquired at the first time point.

The image processor 120 (220) may generate the blended image 630 by performing a weighted sum operation on the T1-weighted image 610 and the FLAIR image 620 acquired at the first time point, and determine a white matter region by using the blended image 630.

T1-weighted imaging, T2-weighted imaging, and FLAIR imaging are techniques for MRI of the brain.

A T1-weighted image shows a difference in signal intensity between tissues due to differences in T1 relaxation times of the tissues. In the T1-weighted image, a difference in signal intensity between a gray matter region and a white matter region is represented as a difference in brightness between the gray and white matter regions.

Referring to FIGS. 6A through 6C, in the T1-weighted image 610, a gray matter region 601 distributed on an outer surface of the brain may be distinguished from a white matter region 603 surrounded by the gray matter region 601. For example, in the T1-weighted image 610 of FIG. 6A, the gray matter region 601 appears darker than the white matter region 603. Thus, the gray matter region 601 may be distinguished from the white matter region 603 according to their brightness in the T1-weighed image 610.

In a normal human, brain tissue in the T1-weighted image 610 may be divided into the gray matter region 601 and the white matter region 603. However, in a normal elderly person with a white matter lesion or a patient with vascular dementia and a white matter lesion, a WMH region 605 may be present in the white matter region 603. If the WMH region 605 is present in the white matter region 603 in the T1-weighted image 610, as shown in FIG. 6A, both the WMH region 605 and the gray matter region 601 may appear darker than the white matte region 603. Thus, because it is hard to accurately distinguish MR signal intensities in the gray matter region 601 and the WMH region 605 from each other, it may be difficult to segment the brain tissue in the T1-weighted image 610 into the gray matter region 601, the white matter region 603, and the WMH region 605, based on only MR signal intensities thereof.

A T2-weighted image shows a difference in signal intensity between tissues due to differences in T2 relaxation times of the tissues. A FLAIR image may be generated based on T2-weighted imaging. In the T2-weighted image, a portion containing a cerebrospinal fluid as well as a WMH region is represented as a high intensity signal. Thus, it may be difficult to distinguish the cerebrospinal fluid from the WMH region in the T2-weighted image. However, because, in the FLAIR image, signal intensity of water may be suppressed by adjusting the T1 relaxation time, only a WMH region may be represented as a high intensity signal.

Referring to FIG. 6B, in the FLAIR image 620, a WMH region 621 may be represented as a white matter high intensity signal. To detect the WMH region 621 in the FLAIR image 620, a white matter region may be defined first. However, because the white matter region may not be easily distinguished from the gray matter region in the FLAIR image 620, the WMH region 621 may be difficult to detect precisely.

In other words, detecting a WMH region directly in a T1-weighted image, a T2-weighted image, or a FLAIR image may cause a slight degradation in accuracy.

The WMH region 621 in the FLAIR image 620 is often found in patients with vascular dementia. A size and distribution of the WMH region 621 in the FLAIR image 620 is associated with symptoms in patients who suffer from dementia, or risk of developing dementia. Thus, precise measurement of the WMH region 621 in the FLAIR image 620 is for diagnosis of patients with dementia.

According to an exemplary embodiment, the WMH region 621 may be detected in the FLAIR image 620 by using the blended image 630 generated by performing a weighted sum operation on the T1-weighted image and the FLAIR image 620. Using the blended image 630 allows accurate classification of brain tissue of a patient with a white matter lesion and precise localization of a WMH region. A method of generating the blended image 630 will now be described in more detail.

To generate the blended image 630, different types of images may be registered first. Among images acquired by performing MRI scans at first and second time points, T1-weighted images at the first and second time points are respectively referred to as 1T and 2T images, and FLAIR images at the first and second time points are respectively referred to as 1F and 2F images. First, non-uniformity of signals in the 1T, 1F, 2T, and 2F images is corrected ("non-uniformity correction"). Then, brain regions are extracted from the 1T, 1F, 2T, and 2F images ("brain region extraction"). The 1T and 1F images at the first time point are linearly registered to each other, and the 2T and 2F images at the second time point are linearly registered to each other, using images of the extracted brain region as an input image. Six degrees of freedom of rigid body transformation may be used for the linear registration.

After the linear registration, a blended image of the 1T and 1F images at the first time point and a blended image of the 2T and 2F images at the second time point may be generated. A blended image may be generated by iteratively performing a weighted sum operation on a T1-weighted image and a FLAIR image with varying weights for the T1-weighted image and the FLAIR image. In detail, a similar white matter region may be defined by performing a morphological operation on a brain region extracted from the blended image. A weighted sum operation may be performed on the T1-weighted image and the FLAIR image until a gradient value of a signal in the blended image has a minimum value. The generated blended images at the first and second time points are referred to as 1TF and 2TF images, respectively.

Figure 7A:
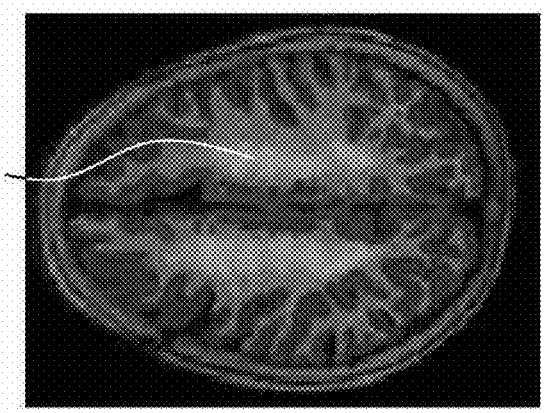
Figure 7B:
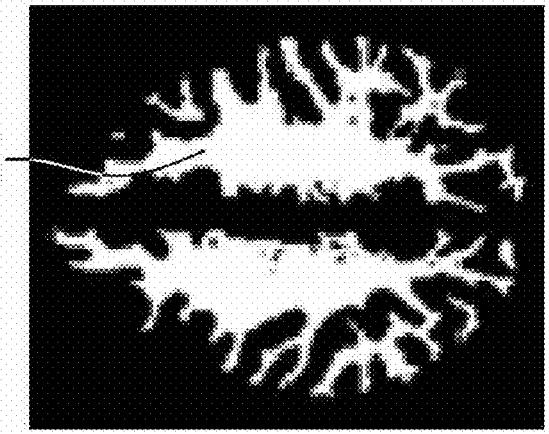
Figure 7C:
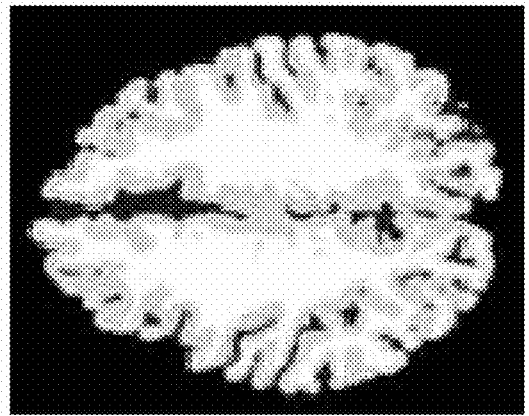

FIGS. 7A through 7C illustrates a process of performing tissue classification on a blended image at a first time point, and defining a white matter region.

FIG. 7A illustrates a tissue classification image 710 at the first time point, FIG. 7B illustrates a white matter region image 720 at the first time point, which is a candidate for a WMH region, and FIG. 7C illustrates an overlay image 730 obtained by overlaying the white matter region image 720 at the first time point over a FLAIR image at the first time point. To obtain a white matter region 721, a 1TF image that is the blended image 630 at the first time point shown in FIG. 6C may be used. By applying an Artificial Neural Network (ANN) algorithm to an input image, tissue classification may be performed to classify the input image according to gray matter, white matter, cerebrospinal fluid, and background. After the tissue classification, tissues may be represented by different brightnesses, as shown in the tissue classification image 710. For example, in the tissue classification image 710, a white matter region, a gray matter region, and background may be indicated in white, gray, and black, respectively.

Among the tissues obtained after the tissue classification, the white matter region may be applied to the FLAIR image 620 at the first time point to determine a white matter region in the FLAIR image 620. The overlay image 730 is obtained by overlaying the white matter region image 720 at the first time point over the registered FLAIR image 620 at the first time point. The white matter region image 720 at the first time point may be used as a mask for detecting a white matter lesion 731 in the FLAIR image 620. Tissue classification may be performed on a blended image at the second time point in the same manner as performed on the blended image 630 at the first time point. A process of normalizing signals at the first and second time points by using a tissue classification image will now be described with reference to FIGS. 8A through 8C.

FIGS. 8A through 8C illustrate a process of normalizing signals at the first and second time points.

FIG. 8A illustrates a T1-weighted image 810, FIG. 8B illustrates an axial view image 820, and FIG. 8C illustrates a sagittal view image 830 of a tissue classification image where a fine gray matter region is defined. Because a gray matter region in a patient with a white matter lesion shows a relatively small change in signal intensity, the gray matter region may be used to extract a signal for normalization. In this case, to extract the gray matter region, a gray matter region in the tissue classification image 710 generated by tissue classification may be used. To prevent errors in signal extraction due to a partial volume effect, an image volume in the gray matter region may be eroded and defragmented by applying a morphological operation. Subsequently, the gray matter region may be skeletonized to extract only fine gray matter regions 821 and 831 in the axial view image 820 and the sagittal view image 830, respectively.

The fine gray matter regions 821 and 831 extracted from the tissue classification image 710 may be used to normalize a signal on their corresponding portions in a FLAIR image. First, an average value and a median value of a signal in fine gray matter regions on FLAIR images (i.e., 1F and 2F images) acquired at the first and second time points are calculated. By compensating for all voxels in the FLAIR images (i.e., 1F and 2F images) at the first and second time points based on the average value and median value, signal intensities on the FLAIR images (1F and 2F images) at the first and second time points may be normalized. Hereinafter, the FLAIR images processed to have normalized signal intensities may be defined as an n1F image (normalized FLAIR image at the first time point) and an n2F image (normalized FLAIR image at the second time point).

Figure 9A:
Figure 9B:
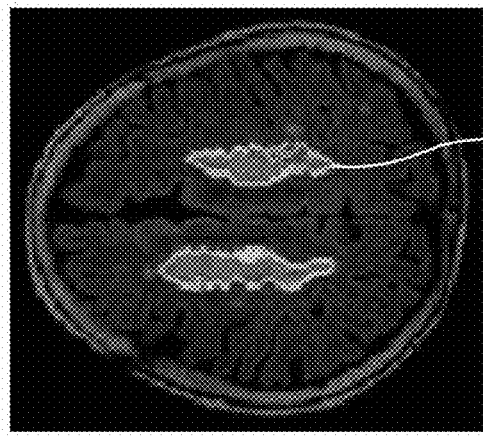
Figure 9C:
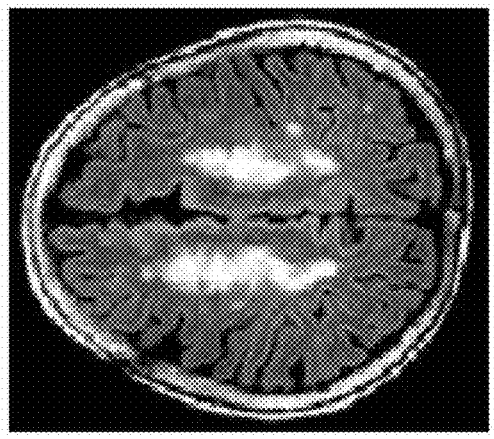

FIGS. 9A through 9C illustrate detection of a WMH region in a normalized FLAIR image. FIG. 9A illustrates a FLAIR image (n1F image) 910 at the first time point on which signal intensity is normalized, FIG. 9B illustrates an n1F image 920 overlaid with a mask 921 of an edge of a WMH region, and FIG. 9C illustrates a gradient image 930.

First, a temporary WMH region is defined using a region having signal intensity corresponding to the 90th percentile in the n1F image 910 and an n2F image as a threshold. Then, adjacent voxels along an edge of the temporary WMH region are segmented into clusters, and a magnitude of a signal is calculated for each cluster. In this case, if a magnitude of a signal for each cluster does not exceed 5% of a sum of magnitudes of signals on the temporary WMH region, the cluster is removed. A morphological operation may be performed to dilate only the remaining temporary WMH region for which a magnitude of a signal exceeds 5% of the sum thereof, and then to subtract the original temporary WMH region, thereby creating the mask 921 on the edge of the WMH region.

Then, the gradient image 930 may be generated using the n1F image 910 and the n2F image. The gradient image 930 shows a brightness corresponding to a gradient value of a signal thereon. An average of gradient values is measured within the defined mask 921. Creation of the mask 921 and measurement of gradient values are iterated by simultaneously changing thresholds of signal intensities on the n1F image 910 and the n2F image, so that the measured average reaches a maximum value. The iteration stops when the average of gradient values reaches a maximum value. In this case, a portion surrounded by the mask 921 may be finally determined as WMH regions on the n1F image 910 and the n2F image.

Linear registration and non-linear registration may be performed on the WMH regions on the n1F image 910 at the first time point and on the n2F image at the second time point to calculate a transform matrix between the n1F image 910 and the n2F image. The WMH region corresponding to the second time point that is later than the first time point may be transformed into an image space at the first time point by using a nearest neighbor distance method. Thus, portions 931, 933, and 935 where a WMH region is newly formed, lost, and maintained, respectively, as compared to a WMH region corresponding to the first time point may be labeled by comparing voxels within the WMH regions corresponding to the first and second time points in the image space at the first time point.

Figure 10:
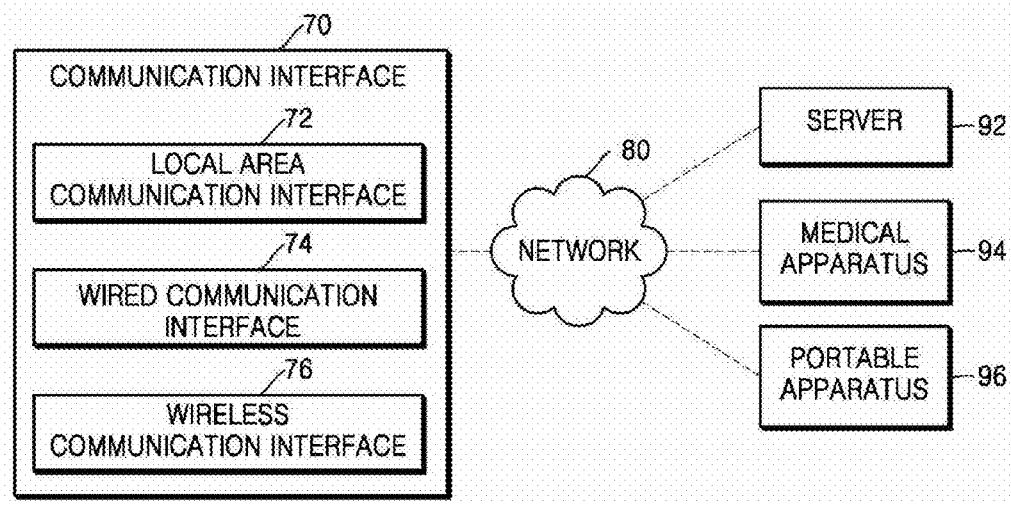
FIG. 10 is a block diagram of a communication interface.

FIG. 10 is a block diagram of a communication interface 70, according to an exemplary embodiment.

The communication interface 70 may transmit and receive data to and from a hospital server or another medical apparatus in a hospital, which is connected through a picture archiving and communication system (PACS), and perform data communication according to the digital imaging and communications in medicine (DICOM) standard.

As shown in FIG. 10, the communication interface 70 may be connected to a network 80 by wire or wirelessly to communicate with a server 92, a medical apparatus 94, and a portable apparatus 96.

In detail, the communication interface 70 may transmit and receive data related to the diagnosis of an object through the network 80, and may also transmit and receive a medical image captured by the medical apparatus 94, such as a CT apparatus, an MRI apparatus, or an X-ray apparatus. In addition, the communication interface 70 may receive a diagnosis history or a treatment schedule of the object from the server 92 and use the same to diagnose the object. The communication interface 70 may perform data communication not only with the server 92 or the medical apparatus 94 in a hospital, but also with the portable apparatus 96, such as a mobile phone, a personal digital assistant (PDA), or a laptop of a doctor or patient.

Also, the communication interface 70 may transmit information about a malfunction of the MRI system or about a medical image quality to a user through the network 80, and receive a feedback regarding the information from the user.

The communication interface 70 may include at least one component enabling communication with an external apparatus.

For example, the communication interface 70 includes a local area communication interface 72, a wired communication interface 74, and a wireless communication interface 76. The local area communication interface 72 refers to a module or interface for performing local area communication with an apparatus within a predetermined distance. Examples of local area communication technology according to an exemplary embodiment include, but are not limited to, a wireless local area network (LAN), Wi-Fi, Bluetooth, ZigBee, Wi-Fi direct (WFD), ultra wideband (UWB), infrared data association (IrDA), Bluetooth low energy (BLE), and near field communication (NFC).

The wired communication interface 74 refers to a module or interface for performing communication by using an electric signal or an optical signal. Examples of wired communication technology include wired communication techniques using a pair cable, a coaxial cable, and an optical fiber cable, and other wired communication techniques.

The wireless communication interface 76 transmits and receives a wireless signal to and from at least one selected from a base station, an external apparatus, and a server in a mobile communication network. Here, the wireless signal may be a voice call signal, a video call signal, or data in any one of various formats according to transmission and reception of a text/multimedia message.

The MRI apparatus 100 (200) of FIG. 1 (2) may be the external server 92, medical apparatus 94, or portable apparatus 96 connected to an MRI system. In other words, the MRI apparatus 100 (200) may be connected to the communication interface 70 shown in FIG. 10 to be operated.

Figure 11:
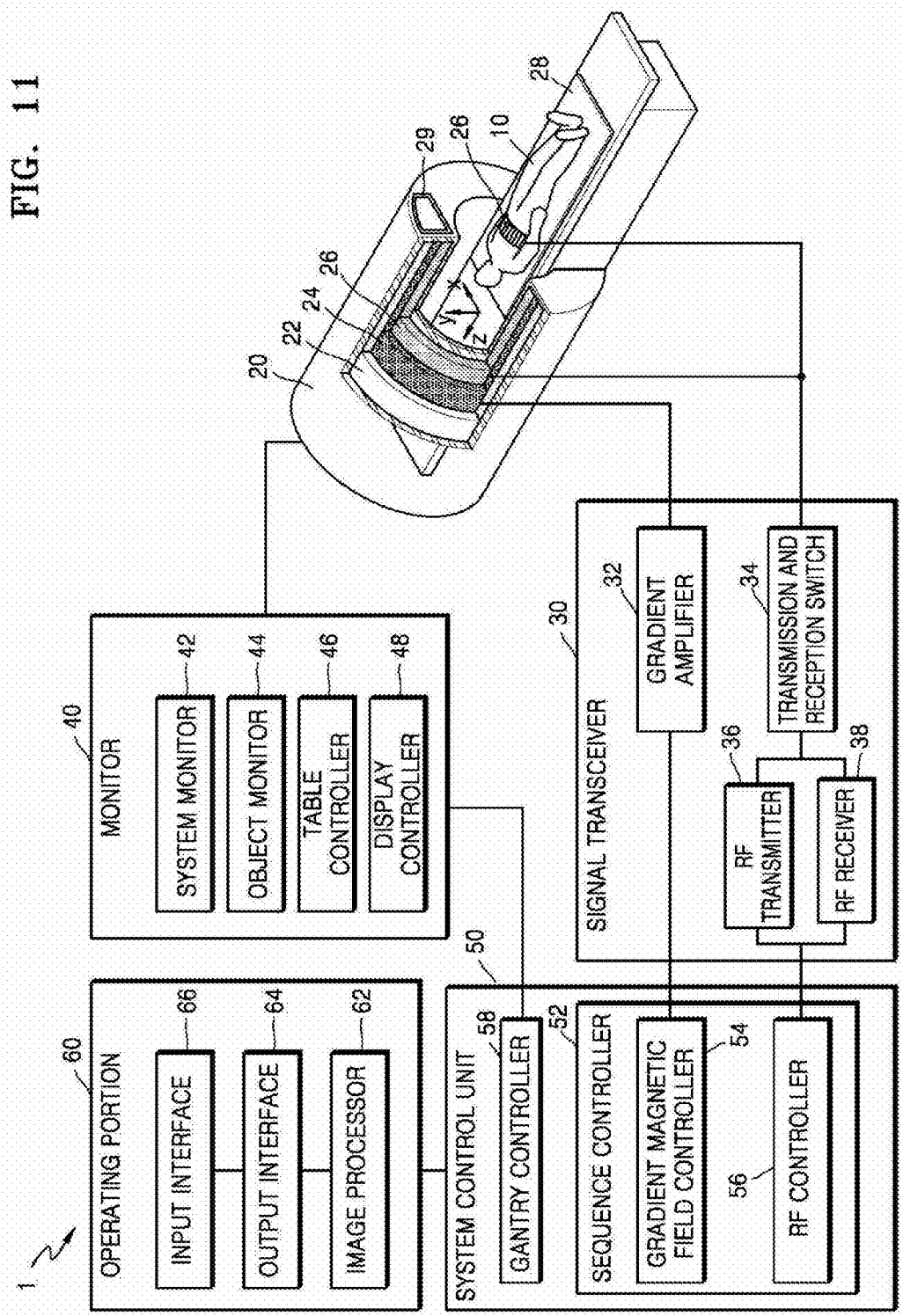
FIG. 11 is a schematic diagram of an MRI system.

FIG. 11 is a block diagram of an MRI system 1.

Referring to FIG. 11, the MRI system 1 may include a gantry 20, a signal transceiver 30, a monitor 40, a system controller 50, and an operating portion 60.

The gantry 20 prevents external emission of electromagnetic waves generated by a main magnet 22, a gradient coil 24, and an RF coil 26. A magnetostatic field and a gradient magnetic field are formed in a bore in the gantry 20, and an RF signal is emitted toward an object 10.

The main magnet 22, the gradient coil 24, and the RF coil 26 may be arranged in a predetermined direction of the gantry 20. The predetermined direction may be a coaxial cylinder direction. The object 10 is disposed on a table 28 that is capable of being inserted into a cylinder along a horizontal axis of the cylinder.

The main magnet 22 generates a magnetostatic field or a static magnetic field for aligning magnetic dipole moments of atomic nuclei of the object 10 in a constant direction. A precise and accurate MR image of the object 10 may be obtained due to a magnetic field generated by the main magnet 22 being strong and uniform.

The gradient coil 24 includes X, Y, and Z coils for generating gradient magnetic fields in X-, Y-, and Z-axis directions crossing each other at right angles. The gradient coil 24 may provide location information of each region of the object 10 by differently inducing resonance frequencies according to the regions of the object 10.

The RF coil 26 may emit an RF signal toward a patient and receive an MR signal emitted from the patient. In detail, the RF coil 26 may transmit, toward atomic nuclei included in the patient and having precessional motion, an RF signal having the same frequency as that of the precessional motion, stop transmitting the RF signal, and then receive an MR signal emitted from the atomic nuclei included in the patient.

For example, to transit an atomic nucleus from a low energy state to a high energy state, the RF coil 26 may generate and apply an electromagnetic wave signal that is an RF signal corresponding to a type of the atomic nucleus, to the object 10. When the electromagnetic wave signal generated by the RF coil 26 is applied to the atomic nucleus, the atomic nucleus may transit from the low energy state to the high energy state. Then, when electromagnetic waves generated by the RF coil 26 disappear, the atomic nucleus to which the electromagnetic waves were applied transits from the high energy state to the low energy state, thereby emitting electromagnetic waves having a Lamor frequency. In other words, when the applying of the electromagnetic wave signal to the atomic nucleus is stopped, an energy level of the atomic nucleus is changed from a high energy level to a low energy level, and thus the atomic nucleus may emit electromagnetic waves having a Lamor frequency. The RF coil 26 may receive electromagnetic wave signals from atomic nuclei included in the object 10.

The RF coil 26 may be realized as one RF transmitting and receiving coil having both a function of generating electromagnetic waves each having an RF that corresponds to a type of an atomic nucleus and a function of receiving electromagnetic waves emitted from an atomic nucleus. Alternatively, the RF coil 26 may be realized as a transmission RF coil having a function of generating electromagnetic waves each having an RF that corresponds to a type of an atomic nucleus, and a reception RF coil having a function of receiving electromagnetic waves emitted from an atomic nucleus.

The RF coil 26 may be fixed to the gantry 20 or may be detachable. When the RF coil 26 is detachable, the RF coil 26 may be an RF coil for a part of the object, such as a head RF coil, a chest RF coil, a leg RF coil, a neck RF coil, a shoulder RF coil, a wrist RF coil, or an ankle RF coil.

The RF coil 26 may communicate with an external apparatus via wires and/or wirelessly, and may also perform dual tune communication according to a communication frequency band.

The RF coil 26 may communicate with an external apparatus via wires and/or wirelessly, and may also perform dual tune communication according to a communication frequency band.

The RF coil 26 may be a transmission exclusive coil, a reception exclusive coil, or a transmission and reception coil according to methods of transmitting and receiving an RF signal.

The RF coil 26 may be an RF coil having various numbers of channels, such as 16 channels, 32 channels, 72 channels, and 144 channels.

The gantry 20 further includes a display 29 disposed outside the gantry 20 and a display disposed inside the gantry 20. The gantry 20 may provide predetermined information to the user or the object 10 through the display 29 and the display respectively disposed outside and inside the gantry 20.

The signal transceiver 30 may control the gradient magnetic field formed inside the gantry 20, i.e., in the bore, according to a predetermined MR sequence, and control transmission and reception of an RF signal and an MR signal.

The signal transceiver 30 includes a gradient amplifier 32, a transmission and reception switch 34, an RF transmitter 36, and an RF receiver 38.

The gradient amplifier 32 drives the gradient coil 24 included in the gantry 20, and may supply a pulse signal for generating a gradient magnetic field to the gradient coil 24 under the control of a gradient magnetic field controller 54. By controlling the pulse signal supplied from the gradient amplifier 32 to the gradient coil 24, gradient magnetic fields in X-, Y-, and Z-axis directions may be synthesized.

The RF transmitter 36 and the RF receiver 38 may drive the RF coil 26. The RF transmitter 36 may supply an RF pulse in a Lamor frequency to the RF coil 26, and the RF receiver 38 may receive an MR signal received by the RF coil 26.

The transmission and reception switch 34 may adjust transmitting and receiving directions of the RF signal and the MR signal. For example, the transmission and reception switch 34 may emit the RF signal toward the object 10 through the RF coil 26 during a transmission mode, and receive the MR signal from the object 10 through the RF coil 26 during a reception mode. The transmission and reception switch 34 may be controlled by a control signal output by an RF controller 56.

The monitor 40 may monitor or control the gantry 20 or devices mounted on the gantry 20. The monitor 40 includes a system monitor 42, an object monitor 44, a table controller 46, and a display controller 48.

The system monitor 42 may monitor and control a state of the magnetostatic field, a state of the gradient magnetic field, a state of the RF signal, a state of the RF coil 26, a state of the table 28, a state of a device measuring body information of the object 10, a power supply state, a state of a thermal exchanger, and a state of a compressor.

The object monitor 44 monitors a state of the object 10. In detail, the object monitor 44 may include a camera for observing a movement or position of the object 10, a respiration measurer for measuring the respiration of the object 10, an electrocardiogram (ECG) measurer for measuring the electrical activity of the object 10, or a temperature measurer for measuring a temperature of the object 10.

The table controller 46 controls a movement of the table 28 where the object 10 is positioned. The table controller 46 may control the movement of the table 28 according to a sequence control of a sequence controller 52. For example, during moving imaging of the object 10, the table controller 46 may continuously or discontinuously move the table 28 according to the sequence control of the sequence controller 52, and thus the object 10 may be photographed in a field of view (FOV) larger than that of the gantry 20.

The display controller 48 controls the display 29 disposed outside the gantry 20 and the display disposed inside the gantry 20. In detail, the display controller 48 may control the display 29 and the display to be on or off, and may control a screen image to be output on the display 29 and the display. Also, when a speaker is located inside or outside the gantry 20, the display controller 48 may control the speaker to be on or off, or may control sound to be output via the speaker.

The system controller 50 includes the sequence controller 52 for controlling a sequence of signals formed in the gantry 20, and a gantry controller 58 for controlling the gantry 20 and the devices mounted on the gantry 20.

The sequence controller 52 may include the gradient magnetic field controller 54 for controlling the gradient amplifier 32, and the RF controller 56 for controlling the RF transmitter 36, the RF receiver 38, and the transmission and reception switch 34. The sequence controller 52 may control the gradient amplifier 32, the RF transmitter 36, the RF receiver 38, and the transmission and reception switch 34 according to a pulse sequence received from the operating portion 60. Here, the pulse sequence includes all information to control the gradient amplifier 32, the RF transmitter 36, the RF receiver 38, and the transmission and reception switch 34. For example, the pulse sequence may include information about a strength, an application time, and application timing of a pulse signal applied to the gradient coil 24.

The operating portion 60 may request the system controller 50 to transmit pulse sequence information while controlling an overall operation of the MRI system 1.

The operating portion 60 includes an image processor 62 for receiving and processing the MR signal received by the RF receiver 38, an output interface 64, and an input interface 66.

The image processor 62 may process the MR signal received from the RF receiver 38 to generate MR image data of the object 10.

The image processor 62 receives the MR signal received by the RF receiver 38 and performs any one of various signal processes, such as amplification, frequency transformation, phase detection, low frequency amplification, and filtering, on the received MR signal.

The image processor 62 may arrange data in a k space (for example, also referred to as a Fourier space or a frequency space) of a memory, and rearrange the digital data into image data via 2D or 3D Fourier transformation.

The image processor 62 may perform a composition process or difference calculation process on image data. The composition process may include an addition process on a pixel or a maximum intensity projection (MIP) process. The image processor 62 may store not only the rearranged image data but also image data on which a composition process or a difference calculation process is performed, in a memory or an external server.

The image processor 62 may perform any of the signal processes on the MR signal in parallel. For example, the image processor 62 may perform a signal process on a plurality of MR signals received by a multi-channel RF coil in parallel to rearrange the plurality of MR signals into image data.

The output interface 64 may output image data generated or rearranged by the image processor 62 to the user. The output interface 64 may also output information for the user to manipulate the MRI system 1, such as a user interface (UI), user information, or object information. Examples of the output interface 64 may include a speaker, a printer, a cathode ray tube (CRT) display, a liquid crystal display (LCD), a plasma display panel (PDP), an organic light emitting diode (OLED) display, a field emission display (FED), a light emitting diode (LED) display, a vacuum fluorescent display (VFD), a digital light processing (DLP) display, a flat panel display (PFD), a three-dimensional (3D) display, a transparent display, and other various output devices.

The user may input object information, parameter information, a scan condition, a pulse sequence, or information about image composition or difference calculation by using the input interface 66. The input interface 66 may be a keyboard, a mouse, a track ball, a voice recognizer, a gesture recognizer, a touch screen, or any one of other various input devices.

The signal transceiver 30, the monitor 40, the system controller 50, and the operating portion 60 are separate components in FIG. 11, but respective functions of the signal transceiver 30, the monitor 40, the system controller 50, and the operating portion 60 may be performed by another component. For example, the image processor 62 converts the MR signal received from the RF receiver 38 into a digital signal in FIG. 11, but alternatively, the conversion of the MR signal into the digital signal may be performed by the RF receiver 38 or the RF coil 26.

The gantry 20, the RF coil 26, the signal transceiver 30, the monitor 40, the system controller 50, and the operating portion 60 may be connected to each other by wire or wirelessly, and when they are connected wirelessly, the MRI system 1 may further include an apparatus for synchronizing clock signals therebetween. Communication between the gantry 20, the RF coil 26, the signal transceiver 30, the monitor 40, the system controller 50, and the operating portion 60 may be performed by using a high-speed digital interface, such as low voltage differential signaling (LVDS), asynchronous serial communication, such as a universal asynchronous receiver transmitter (UART), a low-delay network protocol, such as error synchronous serial communication or a controller area network (CAN), or optical communication.

While not restricted thereto, an exemplary embodiment can be embodied as computer-readable code on a computer-readable recording medium. For example, a control program that controls the above-described operations may be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an exemplary embodiment may be written as a computer program transmitted over a computer-readable transmission medium, such as a carrier wave, and received and implemented in general-use or special-purpose digital computers that execute the programs. Moreover, it is understood that in exemplary embodiments, one or more units can include circuitry, a processor, a microprocessor, etc., and may execute a computer program stored in a computer-readable medium.

The foregoing exemplary embodiments and advantages are examples and are not to be construed as limiting. The present teaching may be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A magnetic resonance imaging (MRI) apparatus comprising:
    a scanner configured to:
        acquire, at a first time point, a first image that is a T1-weighted image and a second image that is a fluid attenuated inversion recovery (FLAIR) image by performing a first MRI scan on a brain; and
        acquire, at a second time point, the first image and the second image by performing a second MRI scan on the brain;
    an image processor configured to:
        determine a white matter region in the second image, based on the first image and the second image; and
        detect a white matter hyperintensity (WMH) region in the determined white matter region; and
    an output interface configured to display the detected WMH region and a generation and a loss of the detected WMH region over time between the first time point and the second time point.

2. The MRI apparatus of claim 1, wherein the output interface is further configured to indicate portions where the WMH region is generated and lost at corresponding locations in the second image.

3. The MRI apparatus of claim 1, wherein the output interface is further configured to:
    display the second image in a first region of a screen; and
    display, as numerical values, a volume of the WMH region and an amount of change in the WMH region over time, in a second region of the screen.

4. The MRI apparatus of claim 1, wherein the generation and the loss of the WMH region over time comprises a change over time in the WMH region in at least one among frontal, parietal, temporal, and occipital lobes.

5. The MRI apparatus of claim 1, further comprising an input interface configured to receive an input selecting at least one among frontal, parietal, temporal, and occipital lobes.

6. The MRI apparatus of claim 5, wherein the output interface is further configured to display a change over time in the WMH region in the selected at least one among frontal, parietal, temporal, and occipital lobes.

7. The MRI apparatus of claim 1, wherein the image processor is further configured to:
    generate a blended image by performing a weighted sum on the first image and the second image; and
    determine the white matter region based on the blended image.

8. The MRI apparatus of claim 1, wherein the image processor is further configured to normalize an intensity of an image signal in each of the second image acquired at the first time point and the second image acquired at the second time point.

9. The MRI apparatus of claim 8, wherein the image processor is further configured to normalize the intensity of the image signal, based on an intensity of an image signal in a gray matter region in each of the second image acquired at the first time point and the second image acquired at the second time point.

10. A method of processing a magnetic resonance (MR) image, the method comprising:
    acquiring, at a first time point, a first image that is a T1-weighted image and a second image that is a fluid attenuated inversion recovery (FLAIR) image by performing a first magnetic resonance imaging (MRI) scan on a brain;
    acquiring, at a second time point, the first image and the second image by performing a second MRI scan on the brain;
    determining a white matter region in the second image, based on the first image and the second image;
    detecting a white matter hyperintensity (WMH) region in the determined white matter region; and
    displaying the detected WMH region and a generation and a loss of the detected WMH region over time between the first time point and the second time point.

11. The method of claim 10, wherein the displaying comprises indicating portions where the WMH region is generated and lost at corresponding locations in the second image.

12. The method of claim 10, wherein the displaying comprises:
    displaying the second image in a first region of a screen; and
    displaying, as numerical values, a volume of the WMH region and an amount of change in the WMH region over time, in a second region of the screen.

13. The method of claim 10, further comprising receiving an input selecting at least one among frontal, parietal, temporal, and occipital lobes.

14. The method of claim 13, wherein the displaying comprises displaying a change over time in the WMH region in the selected at least one among frontal, parietal, temporal, and occipital lobes.

15. The method of claim 10, wherein the determining comprises:
    generating a blended image by performing a weighted sum on the first image and the second image; and
    determining the white matter region, based on the blended image.

16. The method of claim 15, wherein the determining further comprises:
    classifying tissues in the blended image, the tissues comprising another white matter region;
    generating a white matter region image comprising the other white matter region; and
    overlaying the whiter matter region image over the second image to determine the white matter region in the second image.

17. The method of claim 10, wherein the detecting comprises normalizing an intensity of an image signal in each of the second image acquired at the first time point and the second image acquired at the second time point.

18. The method of claim 17, wherein the normalizing comprises normalizing the intensity of the image signal, based on an intensity of an image signal in a gray matter region in each of the second image acquired at the first time point and the second image acquired at the second time point.

* * * * *